(12) United States Patent
Lee et al.

(10) Patent No.: US 7,927,860 B2
(45) Date of Patent: Apr. 19, 2011

(54) ***EBALLISTRA LINEATA* CM602(KCTC 10945BP) AND PHYTASE PRODUCED THEREFROM**

(75) Inventors: Young Kyu Lee, Ansung-si (KR); Seong Hyun Choi, Daejeon (KR)

(73) Assignee: Chung Mi Bio Co., Ltd., Ansung-si (KR)

( * ) Notice: Subject to any disclaimer, the term of this patent is extended or adjusted under 35 U.S.C. 154(b) by 0 days.

(21) Appl. No.: 12/442,485

(22) PCT Filed: Sep. 21, 2007

(86) PCT No.: PCT/KR2007/004634
§ 371 (c)(1),
(2), (4) Date: Jun. 19, 2009

(87) PCT Pub. No.: WO2008/035945
PCT Pub. Date: Mar. 27, 2008

(65) Prior Publication Data
US 2010/0009037 A1    Jan. 14, 2010

(30) Foreign Application Priority Data

Sep. 22, 2006   (KR) .................. 10-2006-0092419

(51) Int. Cl.
*C12N 15/81* (2006.01)
*C12N 9/12* (2006.01)
(52) U.S. Cl. ............... 435/254.2; 435/194; 435/195; 435/254.1
(58) Field of Classification Search .............. 435/195, 435/254.1, 254.2, 194
See application file for complete search history.

(56) References Cited

FOREIGN PATENT DOCUMENTS

| | | |
|---|---|---|
| KR | 10-2001-0003164 A | 1/2001 |
| KR | 10-2002-0000935 A | 1/2002 |

*Primary Examiner* — Tekchand Saidha
(74) *Attorney, Agent, or Firm* — Rothwell, Figg, Ernst & Manbeck, P.C.

(57) ABSTRACT

The present invention relates to a novel yeast strain, *Eballistra lineata* CM602 (KCTC 10945BP) and a phytase produced by the strain. The phytase is thermo- and pH-stable, and also shows a superior enzyme activity at a body temperature of a domestic animal, thus being useful as an additive of forage which may increase the utilization of organic phosphorus. Further, *Eballistra lineata* CM602 (KCTC 10945BP) strain may be used for a mass-production of enzyme by maximizing biosynthesis of phytase by means of gene recombination techniques, fermentation and optimization.

5 Claims, 7 Drawing Sheets

```
>CM-602 (593bp)
CGGCGAGTGAAGCGGGAAGAGCTCAAATTTGAAAGCTGGCTCCTTTAGGTGTCCGCATTGTAATCTCGAGAAGCGT
TTTCCGCGCTGGACCGCGTACAAGTCCCTTGGAATAGGGCATCGTAGAGGGTGAGAATCCCGTACTTGACGCGGCA
GCCAGTGCTTTGTGATACGCTCTCCACGAGTCGAGTTGTTTGGGAATGCAGCTCAAAATGGGTGGTAAATTCCATC
TAAAGCTAAATATTGGGGAGAGACCGATAGCGAACAAGTACCGTGAGGGAAAGATGAAAAGCACTTTGGAAAGAG
AGTTAAACAGTACGTGAAATTGTCGAAAGGGAAGCGCTTGAAGTCAGCTATGTTGTTTGGAATTCAGCCTTGCTTC
TGCATGGTGTACTTTCCTTGTAACAGGCCAGCATCGGTTTCATCGGCCGGATAAGGGTGGGAGGAATGTAGCATCC
TTCGGGATGTGTTATAGCCTCTTACTGGATACGGCTCGACGAGACCGAGGAACGCAGTGCGCCCTCACGGGTGGGC
CCTCGGGCACCTTCGCACTTAGGATGCTGGCGTAATGGCTTTAAGCGGCCCGTCTTGAAACA
//
```

*EBALLISTRA LINEATA* CM602(KCTC 10945BP) AND PHYTASE PRODUCED THEREFROM

CROSS REFERENCE TO RELATED APPLICATIONS

This application is a 35 U.S.C. §371 National Phase Entry Application from PCT/KR2007/004634, filed Sep. 21, 2007, and designating the United States, which claims priority under 35 U.S.C. §119 to Korean Patent Application No. 10-2006-0092419 filed Sep. 22, 2006, which is incorporated herein in its entirety.

TECHNICAL FIELD

The present invention relates to *Eballistra lineata* CM602 (KCTC 10945BP) and a phytase produced by *Eballistra lineata* CM602 (KCTC 10945BP), i.e. a phytase-producing yeast separated from dry pumpkin leaves and the produced phytase having different features from a conventional phytase.

RELATED PRIOR ART

About 75% of phosphorus in vegetable forage exists in the form of phytate [see Cromwell et al., J. Anim. Sci., 71:1831-1840, 1993]. Phytate (myo-inositol 1,2,3,4,5,6,-hexakis dihydrogen phosphate), a compound storing vegetable organic phosphoric acid, is a main ingredient of vegetable forage and is a combination of inositol and phosphate. This is useful for livestock farming [see Maga, J. A., J. Agric. Food Chem., 30:1-9, 1982].

The phytate contained in forage comprises calcium, magnesium, iron or zinc that is chemically combined with myo-inositol hexaphosphate. The phytate serves as an anti-nutritional factor that adsorbs an inorganic ions important to livestock [see Qian et al., J. Anim. Sci., 74:1288-1297, 1996]. The phytate also combines with protein which causes indigestion and lowering the efficiency of forage. Therefore, the decomposition of phytate existing in forage is recommended for the maximum efficiency of forage [see Lei et al., J. Anim. Sci., 71:3368-3375, 1993].

However, monogastric animal such as poultry and a pig does not have phytase which decomposes phytate and isolates phosphoric acid in their digestive organs. Thus, most of the organic phosphorus in forage is excreted through excrement and urine [see Yi et al., Poultry Sci., 75:240-249, 1996].

This phytase (myo-inositol hexakisphosphate phosphohydrolase, EC 3.1.3.8) exists in a plant, microorganism, fungi, etc, and produces myo-inositol and phosphate (free orthophosphate) by hydrolyzing phytate (myo-inositol hexaphosphoric acid) [see Reddy et al., Adv. Food Res., 28:1-92, 1982].

When used as an additive in forage, phytase increases the utilization of organic phosphorus by more than 60% and promotes the intestinal absorption of inorganic matter and the digestion of protein, thereby improving the nutritional value of forage [see Denbow et al., Poultry Sci., 74:1831-1842, 1995].

There are researches which show the genetically modified pig which produces phytase. Golovan et al. reported that a genetically modified pig produced phytase and decreased the phosphorus content in excretion by 75% [Golovan S P et al., Nat Biotechnol 19(8):741-5, 2001].

However, the conventional phytases, separated from a fungus (*Aspergillus ficcum*) or a bacterium (*Bacillus subtilis*), have not been industrially utilized due to the following reasons: (i) a low productivity, (ii) a specific activity and (iii) a low thermal resistance. In particular, fungi require a relatively long cultivation time and delicate fermentation conditions such as ventilation and agitation, thus making the mass production is difficult.

DETAILED DESCRIPTION

The present inventors have exerted extensive efforts to develop a phytase that shows a superior enzyme activity in an animal body when ingested by the animal and is thermo- and pH-stable in the wide range of temperature and pH. As a result, the present invention has been achieved by separating a phytase-producing yeast, i.e. *Eballistra lineata* CM602 from dry pumpkin leaves. The phytase produced by the strain has improved features compared to already known phytases.

In this respect, the main purpose of the current invention is to produce *Eballistra lineata* CM602 (KCTC 10945BP).

Therefore, according to an aspect of the present invention, there is provided a biologically pure stain of *Eballistra lineata* CM602 (KCTC 10945BP).

According to another aspect of the present invention, there is provided a phytase that is produced by the *Eballistra lineata* CM602 (KCTC 10945BP).

According to still another aspect of the present invention, there is provided forage comprising the phytase herein.

According to an embodiment of the present invention, there is provided a phytase that shows a superior enzyme activity in an animal body (at 39° C.) when ingested by the animal and is thermo- and pH-stable in the wide range of temperature and pH.

According to a preferable embodiment of the present invention, there is provided a phytase that shows the best enzymatic activity at 55° C., a sufficient enzyme activity at 39° C. and a superior thermal stability at 70° C.; and shows an optimal enzymatic activity at pH values of 7.0 and 2.0 and maintains higher than 60% of relative activity at pH 3.5-9.0.

Hereunder is provided a detailed description of the present invention. As an attempt to find a microorganism that produces a phytase having a superior phytase activity, thermal stability and pH stability, the present inventors have investigated a phytase-producing strains separated from pig manure, forage, compost, chaff, humus soil, corn cobs, bark of a tree, water plant, smartweed, dry pumpkin leaves, potato leaves, ginseng leaves, pumpkin flower, clay, hay, dry bark of a pine, a pine cone, yellow earth, etc.

As a result, a yeast strain of the present invention, i.e. *Eballistra lineata* CM602 (KCTC 10945BP), was finally obtained, and the separation and the identification are conducted as follows:

(1) First separation of microorganisms having a phytase enzyme activity,
(2) Measurement of enzymatic titer of the first separated microorganisms,
(3) Measurement of the thermal stability and pH stability of the enzymes, and
(4) Identification of the selected strains.

(1) First Separation of Microorganism with Phytase Enzyme Activity

Microorganism that produces a phytase enzyme is separated from various specimens as described below.

According to an embodiment of the present invention, eighty nine (89) kinds of specimen are arranged such as pig manure, forage, compost, chaff, humus soil, corn cobs, bark of a tree, water plant, smartweed, dry pumpkin leaves, potato leaves, ginseng leaves, pumpkin flower, clay, hay, dry bark of a pine, a pine cone, yellow earth, etc.

Each specimen is added in sterilized physiological saline solution and diluted. PDA (potato dextrose agar) plate medium containing 0.1-0.3% phytate, 0.1-0.2% tartaric acid and a small amount of $CaCl_2$ was prepared.

One drop of the diluted solution is spread on a PDA plate medium, and allowed to be well absorbed to the medium surface, followed by cultivation at 25-37° C. for 2-3 days. Phytase activity is determined by applying a solution containing staining agent onto cluster of microorganism. The solution is prepared by mixing 10% ascorbic acid, 2.5% ammonium molybdate, 2N $H_2SO_4$ and 5% TCA in the weight ratio of 1:1:3:0.5. Specimen is considered to be phytase-active if perimeter of the cluster turns blue from the initial color of yellow, and those strains are selected by the first screening.

(2) Measuring Enzyme Titer of the Separated Microorganism

The first screened microorganisms are grown on liquid or solid medium, and strains with a relatively high enzymatic activity are selected by measuring phytase enzymatic activity of the culture filtrate.

The first screened eighty two kinds of strains are inoculated onto phytase-producing medium such as a wheat bran extraction medium and shake-cultivated at 30-40° C. for 2-4 days. Supernatant is separated by a centrifugation, and the supernatant may be used as a crude enzyme solution for measuring the activity of enzyme.

Alternatively, the first screened microorganisms are grown on a PDA plate medium, and the grown yeast cells are collected and suspended in a buffer solution such as 0.1 M sodium acetate buffer solution (pH 5.5). Cell walls are destroyed by the Zymolyase enzyme treatment, and supernatant obtained by centrifugation is used as intracellular fraction enzyme solution for measuring phytase activity.

Strains with a relatively high phytase activity are selected by measuring the phytase enzyme activity (enzyme titer) with the crude enzyme solution or the intracellular fraction enzyme. The measurement of phytase enzyme activity is conducted according to the conventional method.

According to an embodiment of the present invention, sodium phytate solution is prepared by adding 1.0 mM $CaCl_2$ in sodium phytate. The concentration and pH of solution is adjusted to 0.0051 M and 5.5, respectively in acetic acid buffer solution. The sodium phytate solution (0.5 mL) is added in a tube for centrifugation, and stored at 37° C. for 5 minutes, and added with the crude enzyme solution (50 μL) before the reaction is conducted at 37° C. for 30-60 minutes.

The reaction is terminated by adding 0.45 mL of a terminating solution, which is prepared by mixing 25 mL of AM solution, 25 mL of AV solution and 16.5 mL of nitric acid to make total volume to 100 mL, before placing the solution at room temperature for 10 minutes. The resulting reaction solution is centrifuged at 5,000 rpm for 10 minutes, and the absorbance of the obtained supernatant is measured at 415 nm of wavelength by using a spectrophotometer. The content of $PO_4$ is calculated based on a calibration curve obtained by using $NaH_2PO_4$. The enzyme unit, FTU (Measurement for enzyme activity by Natuphos, BASF, Germany), is defined as the amount of enzyme that may separate 1 μmol of phosphate from 5.10 mM sodium phytate solution for one minute at 37° C. The phytate enzyme activity of the crude enzyme solution or the intracellular fraction enzyme solution is calculated into this unit.

(3) Measuring Thermal Stability and pH Stability

Thermal stability and pH stability (resistance to acid) are investigated by using a crude enzyme solution or an intracellular fraction enzyme contained in the screened strains with a relatively high phytase activity.

The thermal stability is determined by measuring the enzymatic activity at various temperatures, particularly at a relatively high temperature. The pH stability is determined by measuring enzymatic activity at various pH values, in particular at a relatively low pH values.

(4) Identification of Selected Strain

The screened strains are identified by investigating the carbon source utilization and determining whether an enzyme is produced or not by using an API kit after the morphological observation.

DNA is separated from yeast cells for the biological identification. Certain genes such as rDNA of ITS (internal transcribed spacer) in ribosome, which is suitable for preparing a phylogenetic tree, is PCR-amplified. The homology level is obtained by comparing the resulting DNA sequence to the reported sequences.

As illustrated above, a certain strain, named strain CM602, is ascertained as superior in the phytase activity, thermal stability and pH stability. The selected CM602 strain grown on a PDA medium is light yellowish and has a cream-like property like a typical yeast. The strain CM602 has a shape of a peanut hull with two endospores. The selected strain uses L-arabinose, D-ribose, D-glucose, D-fructose, D-mannose, D-mannitol, D-maltose, etc, as a carbon source (Table 1), shows a positive activity for an alkaline phosphatase, an acidic phosphatase, an esterase, a lipase, a leucine arylamidase and β-glucosidase (Table 2).

Figure 2:
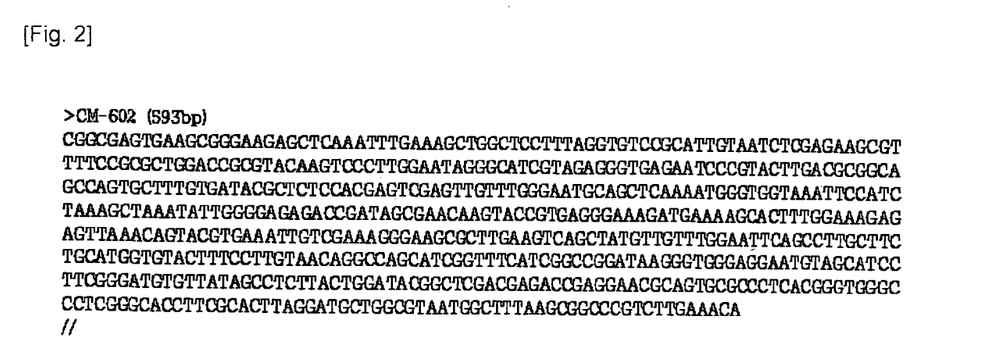
FIG. 2 ITS sequence of ribosomal DNA in Eballistra lineata CM602 (KCTC 10945BP) (SEQ ID NO: 1).
Figure 3:
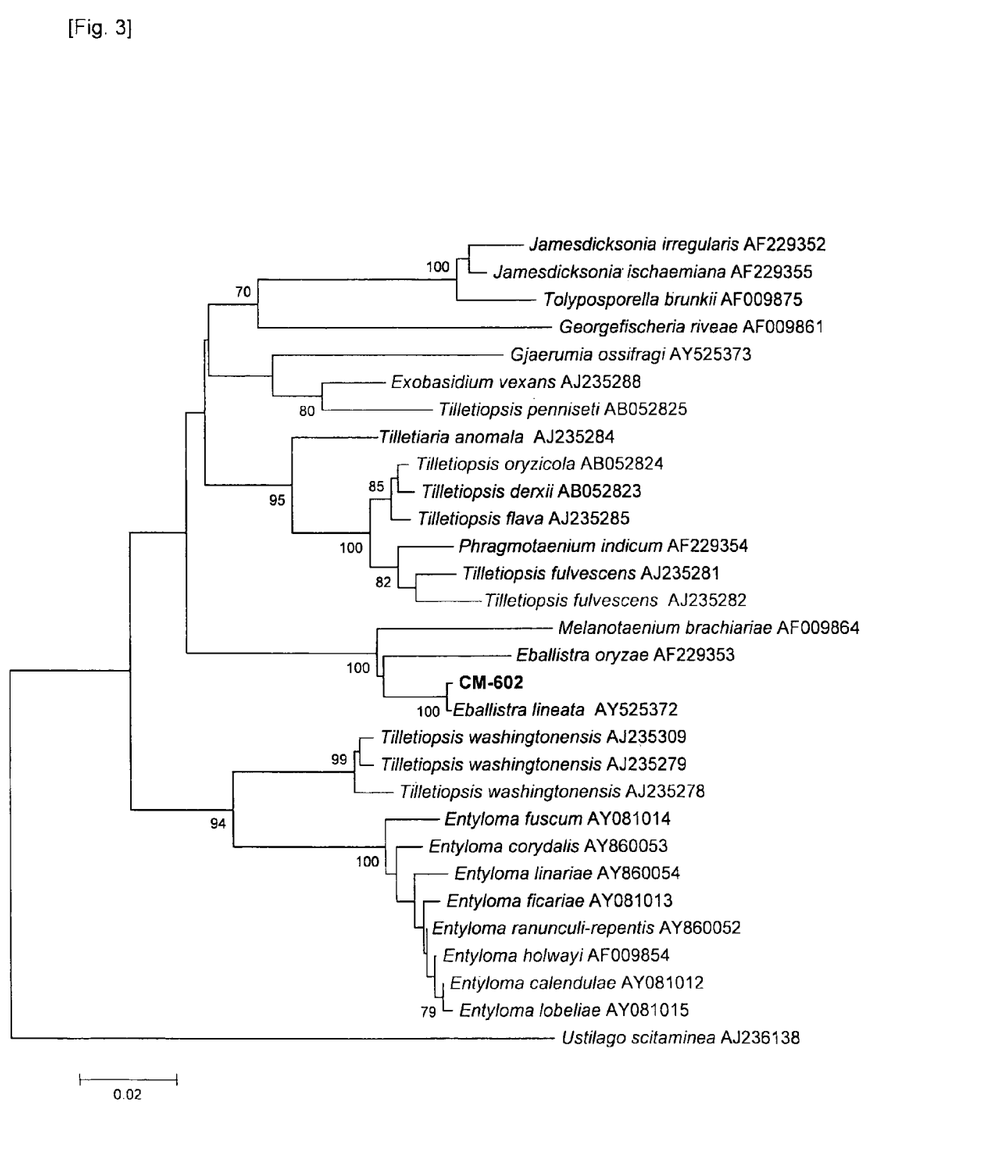
FIG. 3 is a phylogenetic tree of *Eballistra lineata* CM602 (KCTC 10945BP).

Libosome DNA ITS (internal transcribed spacer) sequence of the CM602 strain is analyzed (FIG. 2), and a microorganism phylogenetic tree is prepared according to a neighbor-joining method for the identification of the CM602 strain (FIG. 3).

Based on the morphologic and biochemical analyses along with the gene analysis of libosome DNA ITS gene as described herein, the strain CM602 has been finally determined as *Eballistra lineata*. The CM602 was deposited at the gene bank (Korean Collection for Type Cultures; KCTC) of Biological Resource Center in Korea Research Institute of Bioscience and Biotechnology on May 19, 2006, and endowed with the deposition number of KCTC 10945BP.

Figure 4:
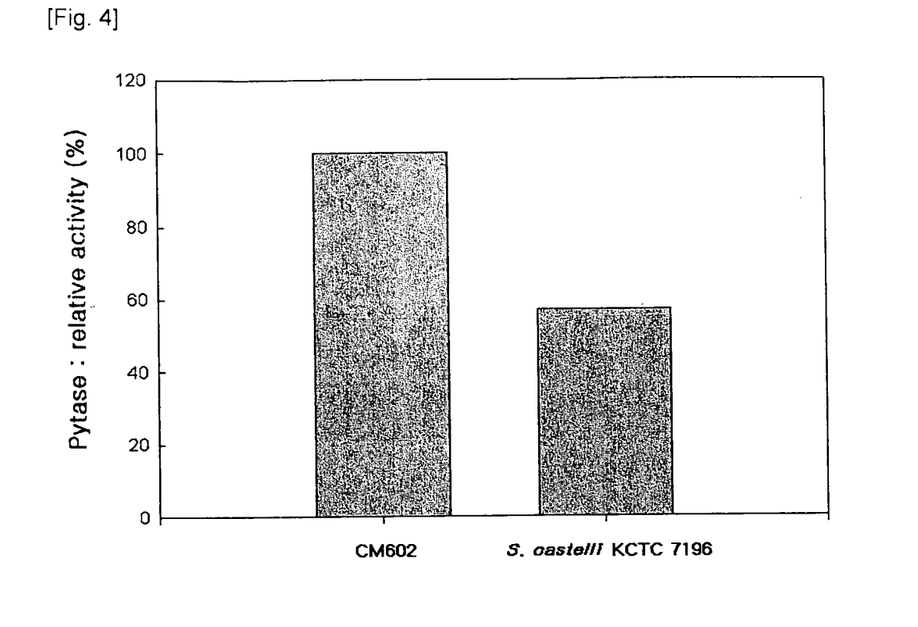
FIG. 4 is a graph, which compares the activities of the phytases produced by *Eballistra lineata* CM602 (KCTC 10945BP) strain and *Schwanniomyces castelli* KCTC 7196.

The *Eballistra lineata* CM602 strain herein shows about twice greater phytase enzyme activity compared to *Schwanniomyces castelli* KCTC 7196 strain, which is known as a phytase-producing yeast strain (FIG. 4).

Figure 5:
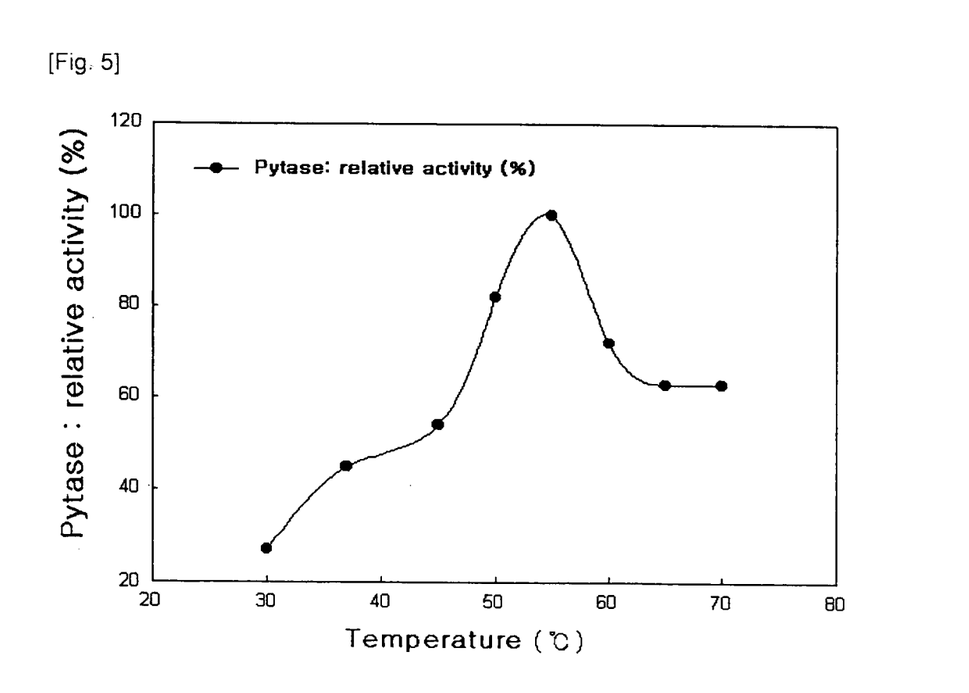
FIG. 5 is a graph which shows a temperature-dependent enzyme activity of the phytase produced by *Eballistra lineata* CM602 (KCTC 10945BP) strain.
Figure 6:
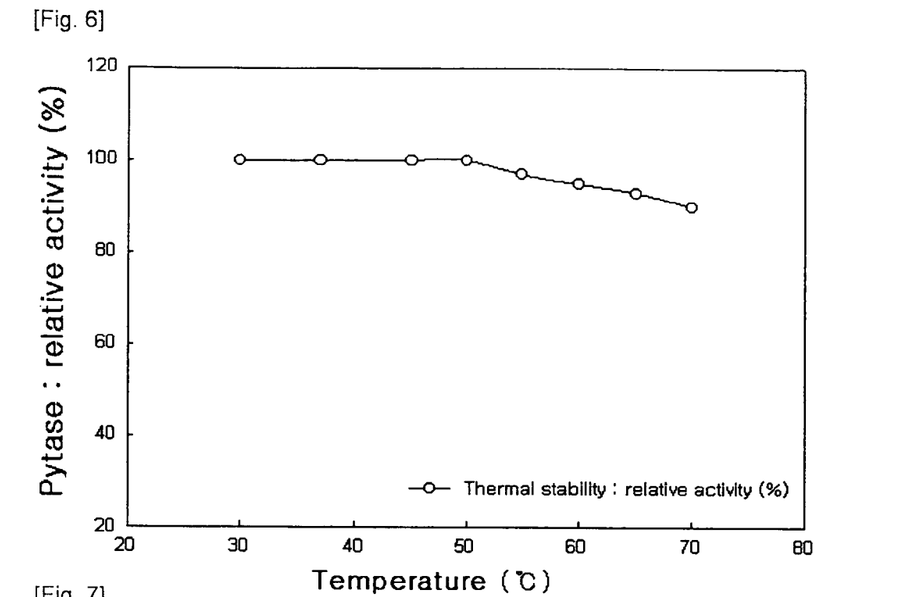
FIG. 6 is a graph which shows a temperature-dependent thermal stability of a phytase produced by *Eballistra lineata* CM602 (KCTC 10945BP) strain.

Further, the phytase produced by the CM602 strain shows a relatively high activity in the temperature range of 50-60° C., and the highest activity at 55° C. (FIG. 5). The phytase shows about 50% relative activity at 39° C., i.e. around the temperature in a body of an animal. Further, the enzyme activity was measured at 37° C. after the thermal treatment at the temperature ranging from 30° C. to 70° C. The results show that the phytase produced by the *Eballistra lineata* CM602 strain shows 90% of the remaining enzyme activity even after the thermal treatment at 70° C. (FIG. 6).

Figure 7:
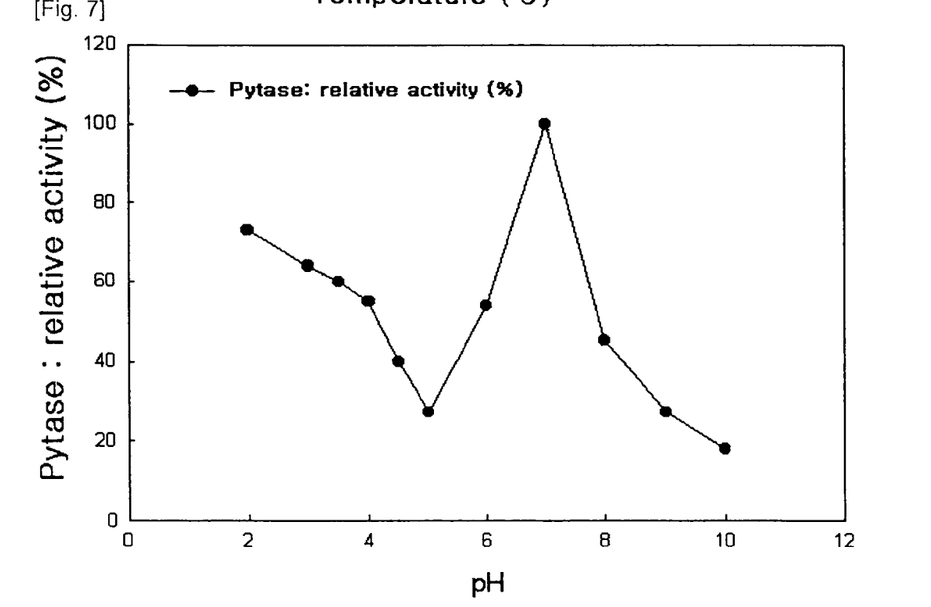
FIG. 7 is a graph which shows a pH-dependent enzyme activity of the phytase produced by *Eballistra lineata* CM602 (KCTC 10945BP) strain.
Figure 8:
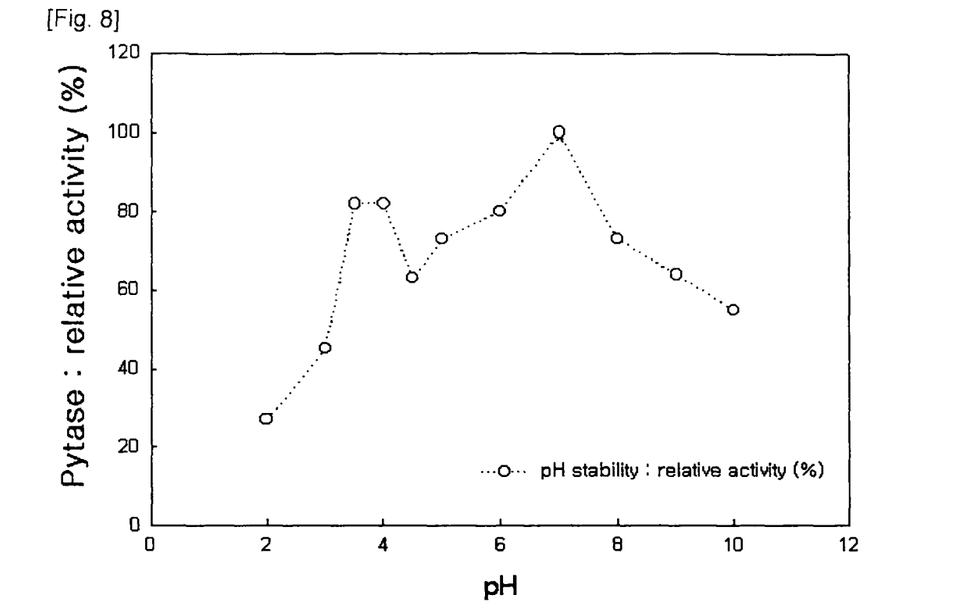
FIG. 8 is a graph which shows a pH-dependent pH-stability of the phytase produced by *Eballistra lineata* CM602 (KCTC 10945BP) strain.

The phytase produced by the *Eballistra lineata* CM602 strain shows a relatively high phytase enzyme activity at pH values of 2.0 and 7.0, and the highest peak at pH 7.0 (FIG. 7). Further, the enzyme activity was measured at 55° C. after the treatment at the pH ranging from 2.0 to 10.0. The results show that the phytase produced by the *Eballistra lineata* CM602 strain shows 80% of the remaining enzymatic activity even after the treatment at pH 3.5-4.0 (FIG. 8).

Therefore, a phytase herein may show a superior activity in the body of animal. It endures a high temperature condition during a forage-manufacturing process and a severely acidic condition such as inside the stomach of an animal, thus remarkably increasing the utilization of organic phosphorus.

A phytase herein may also be prepared by cultivating a phytase-producing *Eballistra lineata* CM602 strain herein, followed by the conventional separation and purification of yeast cells or culture.

As described above, *Eballistra lineata* CM602 (KCTC 10945BP) is a novel bacterial species, and a phytase produced by the strain is also different from the conventional phytase.

The phytase produced by *Eballistra lineata* CM602 (KCTC 10945BP) strain is industrially useful as an additive of forage. This is due to the aforementioned superior phytase enzyme activity, thermal stability and pH stability.

Further, *Eballistra lineata* CM602 (KCTC 10945BP) strain may be used for the biosynthesis of the enzyme on a large scale by using genetic recombination techniques, fermentation and optimization.

A phytase herein may be produced by finding out the phytase genes in *Eballistra lineata* CM602 strain, identifying the genetic features and incorporating the genes into a vector (e.g. a vector from yeast), followed by the expression of the genes. The production may be increased by improving the expression mechanism. Genes from fungi or yeast are better compared to the genes from bacteria for a vector from yeast, and *Eballistra lineata* is useful in this respect.

Further, a phytase produced by *Eballistra lineata* CM602 shows a superior phytase activity when ingested by an animal, enables the utilization of organic phosphate that exists as a phytate, thereby supplementing nutritive elements, decreasing phosphorus discharge and reducing the green tide caused by microalgae.

EXAMPLES

The present invention is described more specifically by the following Examples. Examples herein are meant only to illustrate the present invention, but in no way to limit the scope of the claimed invention.

Example 1

Separation and Identification of Microorganism that Produces Phytase Enzyme, and Ascertaining the Enzyme Activity 1) First Screening of Microorganism Having Phytase Enzyme Activity Microorganism that produces a phytase enzyme was separated from various specimens as described below.

PDA (potato dextrose agar) plate medium containing 0.2% phytate, 0.16% tartaric acid and a small amount of $CaCl_2$ was prepared. Eighty nine (89) kinds of specimen were also arranged such as pig manure, forage, compost, chaff, humus soil, corn cobs, bark of a tree, water plant, smartweed, dry pumpkin leaves, potato leaves, ginseng leaves, pumpkin flower, clay, hay, dry bark of a pine, a pine cone, yellow earth, etc.

Each specimen was added in a sterilized physiological saline solution, and diluted $10^3$-fold. One drop of the diluted solution was spread on a PDA plate medium, and allowed to be well absorbed into the medium surface, followed by the cultivation at 30° C. for 2-3 days with upside down. Phytase activity was determined by applying a solution containing staining agent onto cluster of microorganism. The solution was prepared by mixing 10% ascorbic acid, 2.5% ammonium molybdate, 2N $H_2SO_4$ and 5% TCA by the ratio of 1:1:3:0.5. Specimen was considered as phytase-active if the perimeter of the cluster turns blue from the initial color of yellow, and eighty two (82) kinds of strains were selected by the first screening.

2) Selection Superior Strain Based on Enzyme Titer

Wheat bran extraction medium was prepared by mixing 200 g of wheat bran and 20 g of oil-removed soybean powder with 1,500 mL of tab water at the room temperature for 6 hours and filtering by gauze, followed by addition of 5% molasses and sterilization.

The first screened eighty two kinds of strains were inoculated onto the wheat bran extraction medium and shake-cultivated at 30° C. for 3 days. Supernatant was separated by the centrifugation at 5,000 rpm for 10 minutes, and the supernatant was used as a crude enzyme solution for measuring the enzyme activity as described below.

Measurement of Enzyme Activity

Phytase activity was measured and quantified by using the supernatant of the cultivated microorganism broth or the intracellular fraction enzyme, which is a supernatant obtained after disintegration of cell wall and centrifugation as described below.

Sodium phytate solution was prepared by adding 1.0 mM $CaCl_2$ and sodium phytate, and adjusting the concentration to 0.0051 M and pH 5.5, respectively in acetic acid buffer solution. Substrate containing 0.5 mL of the sodium phytate solution was added in a tube for centrifugation, and stored at 37° C. for 5 minutes. The crude enzyme solution (50 μL) was added and the reaction was conducted at 37° C. for 30-60 minutes. The reaction was terminated by adding 0.45 mL of a terminating solution, which was prepared by mixing 25 mL of AM solution, 25 mL of AV solution and 16.5 mL of nitric acid to make a total volume of 100 mL, before placing the solution at room temperature for 10 minutes. The resulting reaction solution was centrifuged at 5,000 rpm for 10 minutes, and the absorbance of the obtained supernatant was measured at 415 nm by using spectrophotometer. The content of $PO_4$ was calculated based on a calibration curve obtained by using $NaH_2PO_4$. The enzyme unit, FTU (Measurement for enzyme activity by Natuphos, BASF, Germany), is defined as the amount of enzyme that may separate 1 μmol of phosphate from 5.10 mM sodium phytate solution for one minute at 37° C. As used herein, AM solution is referred to as a solution prepared by adding ammonia water in 10% ammonium molybdate solution so that the concentration of the ammonia water is to be 1.0%. As used herein, AV solution is referred to as a solution prepared by dissolving 0.235 g of ammonium vanadate in water and adding 2.0 mL of 35% nitric acid solution so that the total volume is to be 100 mL. The two solutions are stored in a brown bottle.

Strains that produce thermally stable enzymes were selected by testing a crude enzyme solution according to the enzyme activity test method after storing the crude enzyme solution was stored at 70° C. for 15 minutes. As a result, CM602 strain was selected as a strain having the highest activity. Phytase activity test was conducted at the level of crude enzyme solution, and the CM602 strain was ascertained to have an activity of 0.1 unit/mL.

For the intracellular enzyme activity of the strain, yeast cells which were grown on a potato dextrose agar (PDA) plate medium were collected and treated with Zymolyase enzyme for breaking cell walls after the fungal bodies were suspended in 0.1 M sodium acetate buffer solution (pH 5.5), followed by the centrifugation at 5,000 rpm for 20 minutes. After the centrifugation, the supernatant was used as an intracellular fraction, and the phytase activity was analyzed and quantified as illustrated above. The intracellular enzyme activity of CM602 strain was 0.42 unit relative to one gram (wet weight) of a yeast cells.

3) Identification of Selected CM602 Strain
3-1) Morphological Property

Figure 1:
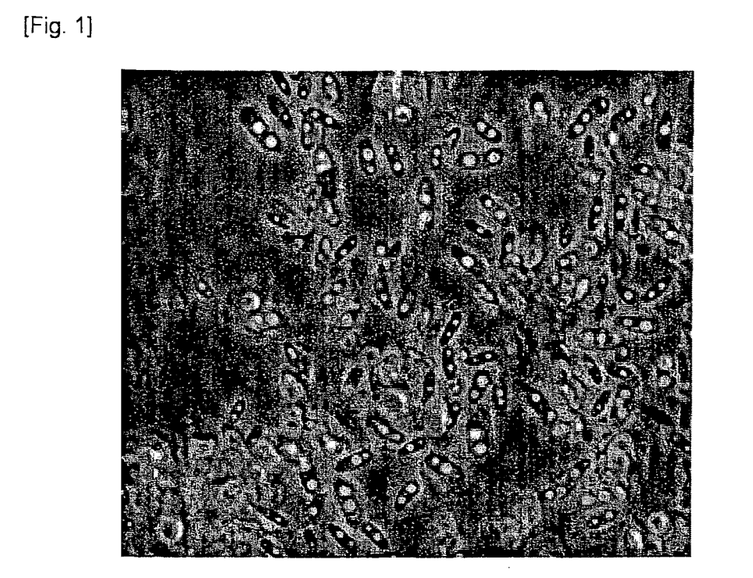
FIG. 1 is an electron micrograph of *Eballistra lineata* CM602 (KCTC 10945BP).

The selected CM602 strain was grown on a PDA medium, and the colony was observed to be of light yellow and have a cream-like property like a typical yeast. Morphological property of yeast cells was observed by an optical microscope, and the result is presented in FIG. 1. The strain CM602 was ascertained to have a shape of a peanut hull with two endospores.

3-2) Biochemical Property

Fermentation inspection was conducted by using API kit (BioMerieux company), and the result is presented in Table 1. The CM602 strain was ascertained to use L-arabinose, D-ribose, glucose, fructose, mannose, mannitol, maltose, sucrose, trehalose, raffinose or L-arabitol as a carbon source (Table 1).

As a result of experiment using API ZYM kit (BioMerieux company), a positive activity of the CM602 strain was detected for alkaline and acid phosphatase, a lipase and a β-glucosidase, which shows that the CM602 strain produces and secretes the aforementioned enzymes (Table 2).

TABLE 1

| Carbon source | CM602 strain |
| --- | --- |
| Glycerol | − |
| Erythritol | − |
| D-Arabinose | − |
| L-Arabinose | + |
| D-Ribose | + |
| D-Xylose | − |
| L-Xylose | − |

TABLE 1-continued

| Carbon source | CM602 strain |
| --- | --- |
| D-Adonitol | − |
| Methyl-β-D-xylose | − |
| D-Galactose | − |
| D-Glucose | + |
| D-Fructose | + |
| D-Mannose | + |
| Sorbose | − |
| L-Rhamnose | − |
| Dulcitol | − |
| Inositol | − |
| D-Mannitol | + |
| D-Sorbitol | − |
| Methyl-α-D-Mannopyranoside | − |
| Mehtyl-α-D-Glucopyranoside | − |
| N-Acetyl-Glucosamine | − |
| Amygdalin | − |
| Arbutin | − |
| Esculin ferric citrate | − |
| Salicin | − |
| D-Cellobiose | − |
| D-Maltose | + |
| D-Lactose | − |
| D-Melobiose | − |
| D-Saccharose (sucrose) | + |
| D-Trehalose | + |
| Inulin | − |
| D-Melezitose | − |
| D-Raffinose | + |
| Amidon | − |
| Glycogen | − |
| Xylitol | − |
| Gentiobiose | − |
| D-Turanose | − |
| D-Lyxose | − |
| D-Tagatose | − |
| D-Fucose | − |
| L-Fucose | − |
| D-Arabitol | − |
| L-Arabitol | + |
| Gluconate (potassium) | − |
| 2-Ketogluconate (potassium) | + |
| 5-Ketogluconate (potassium) | − |

TABLE 2

| Enzyme | CM602 strain |
| --- | --- |
| Alkaline phosphatase | + |
| Esterase (C4) | + |
| Esterase lipase (C8) | + |
| Lipase (C14) | − |
| Leucine arylamidase | + |
| Valine arylamidase | − |
| Crystine arylamidase | − |
| Trypsin | − |
| A-Chymotrypsin | − |
| Acid phosphatase | + |
| Naphtol-AS-BI-phosphohydrolase | − |
| A-Galactosidase | − |
| B-Galactosidase | − |
| β-Glucuronidase | − |
| α-Glucosidase | − |
| β-Glucosidase | + |
| N-Acetyl-β-glucosaminidase | − |
| A-Mannosidase | − |
| α-Fucosidase | − |

3-3) rDNA Analysis of Selected CM602 Strain

The analysis of ITS rDNA was conducted for the identification of the CM602 strain on the level of gene. DNA was separated from yeast cells by using a commercial kit (Solgent Co., Ltd, Korea), and two kinds of following primers were used for amplifying ITS rDNA genes, followed by a sequence analysis [see Im et al. Int. J. Syst. Evol. Microbiol 54, 851-855, 2004):

```
SEQ ID NO: 2:
pITS-F 5'-GTCGTAACAAGGTTAACCTGCGG-3'

SEQ ID NO: 3:
pITS-R 5'-TCCTCCGCTTATTGATAT GC-3'.
```

Ribosome DNA, ITS sequence of CM602 strain was also analyzed, and the result is presented in FIG. 2 and the attached SEQ ID NO: 1. The resulting sequence was sorted using Clustal X program [see Thompson et al. Nucleic acids Res., 24, 4876-4882, 1997], and a microorganism phylogenetic tree prepared according to a neighbor-joining method [see Saitou and Nei, Mol. Bio. Evol. 4, 406-425, 1987] is presented in FIG. 3. The CM602 strain was identified and classified as *Eballistra lineata* or its allied strain (related taxa) (FIG. 3). The homology level was 99.5%.

Based on the aforementioned morphologic and biochemical analyses along with the gene analysis of ribosome DNA ITS gene, the strain CM602 was finally determined as *Eballistra lineata*. The CM602 was deposited at the gene bank (Korean Collection for Type Cultures; KCTC) of Biological Resource Center in Korea Research Institute of Bioscience and Biotechnology on May 19, 2006, and endowed with a deposition number of KCTC 10945BP.

4) Measurement of Phytase Enzyme Activity of CM602 Strain

Comparative test of phytase activity was conducted as follows by using *Eballistra lineata* CM602 (KCTC 10945BP) strain and a reference yeast strain, *Schwanniomyces castellii* KCTC 7196 [Segueilha, L. et al., J. Fermen. Bioeng. 74, 7-11, 1992].

As illustrated in 2) above, the two strains were inoculated onto a wheat bran extraction medium, and shake-cultivated at 30° C. for 3 days. Supernatant was separated by centrifugation, and used as a crude enzyme solution for measuring an enzyme activity at 37° C. As shown in FIG. 4, the *Eballistra lineata* CM602 strain showed about twice higher phytase enzyme activity compared to the KCTC 7196 strain.

5) Measurement of Properties of Phytase

① Activity of Phytase Depending on Temperature

Optimum temperature was obtained by reacting substrate and the crude enzyme solution prepared 4) above in 0.1 M acetic acid buffer solution (pH 5.5) for 60 minutes, respectively, at the temperature range of 30-70° C., followed by the measurement of phytase activity.

As shown in FIG. 5, the phytase produced by CM602 strain showed a relatively high activity at the temperature range of 50-60° C. and the highest activity at 55° C. The phytase showed about 50% relative activity at 39° C., i.e. around the body temperature of animal. This result ascertains that the phytase produced by CM602 strain may exert superior enzymatic activity when ingested by an animal.

② Thermal Stability of Phytase Depending on Temperature

Each crude enzyme solution (50 μL) prepared in 4) above was placed at 30, 40, 50, 60, 70° C., respectively, for 15 minutes. Remaining enzyme activity was obtained by reacting substrate and a crude enzyme solution for 60 minutes at 37° C. as described above before measuring phytase activity.

The phytase activity of a control group, i.e. non-treated group, was measured by reacting a crude enzyme solution with substrate at 37° C. for 60 minutes without a thermal treatment. The relative activity was calculated by the following formula.

$$\text{Relative activity (\%)} = 100 \times \frac{\text{Enzymatic activity of the treated group}}{\text{Enzymatic activity of the non-treated group}}$$

As shown in FIG. 6, the thermal stability of the phytase produced by the CM602 strain decreases as a temperature increases. The CM602 strain shows a relatively high thermal stability, i.e. 90% of activity at 70° C.

The phytase may be useful in the industry because this superior thermal stability is useful in overcoming the declining a heat-induced enzyme activity during the process of pelleting feed or expanding forage.

Thermal stability and optimum temperature of other phytase enzymes were also measured. As a comparative strain [see Segueilha, L. et al., J. Ferment. Bioeng., 74, 7-11, 1992], *Schwanniomyces castelli* KCTC 7196 showed a relatively high thermal stability (77° C.). However, the enzyme activity at a body temperature of an animal (39° C.) is about 20% of the optimum activity, which is lower than 50% of the CM602 strain.

③ Activity of Phytase Depending on pH

Optimum pH value was measured by reacting each crude enzyme solution (50 μL) prepared in 4) above with a substrate solution in acetic acid buffer solution with various pH values in the range of 2.0-10.0 for 60 minutes at 55° C., and measuring a phytase activity.

There were two peaks observed as shown in FIG. 7, i.e. at pH 2.0 and 7.0, and the highest activity was measured at pH 7.0.

④ Stability of phytase depending on pH

Each crude enzyme solution (0.5 mL) prepared in 4) above was stored after adjusting pH in the range of form 2.0 to 10.0, respectively, at 8° C. for 20 hours. 50 μL was taken from the solutions, and reacted with the substrate solution (pH 7.0) at 55° C. for 60 minutes. Remaining enzyme activity was measured, and converted into a relative activity.

The phytase activity of a control group, i.e. non-treated group, was measured by reacting crude enzyme solution with substrate at 55° C. and pH 7.0 for 60 minutes without an acidic treatment. The relative activity was calculated by the following formula.

$$\text{Relative activity (\%)} = 100 \times \frac{\text{Enzymatic activity of the treated group}}{\text{Enzymatic activity of the non-treated group}}$$

The phytase activity was 80% of the maximal enzyme activity at pH values of 3.5 and 4.0, and greater than 60% of the maximal enzyme activity in the range of pH of 3.5-9.0 (FIG. 8). The CM602 strain was ascertained as relatively more pH stable than the reference strain, i.e. *Schwanniomyces castelli* KCTC 7196.

*Schwanniomyces castellii* has also been reported as a phytase-producing yeast [see Segueilha et al. J. Ferm. Bioeng. 74, 7-11, 1992]. It has been known that the phytase produced by *Sch. castellii* shows the optimum pH of 4.4, optimum temperature of 77° C., and is thermally stable at the temperature up to 74° C. An enzyme for a monogastric animal should show a superior enzymatic activity in its digestive organ, i.e. at the temperature of about 39° C. In this respect, the *Sch. castellii* is not preferred as its activity at 39° C. is only 20% of its optimum activity (77° C.).

However, the phytase according to the present invention shows the following advantages as an forage additive: (i) the activity at 39° C. amounts to about 50% of the optimum activity; (ii) the phytase remains thermally stable even at 70° C.; and (iii) the pH stability at pH 3.5-9.0 shows 60% or higher of the optimum activity.

6) Purification of Phytase

The CM602 solution (10 mL) was inoculated onto 2 L of YM medium (Difco), and shake-cultivated at 30° C. for 48 hours before the centrifugation (10,000×g, 15 minutes). The collected yeast cells were broken or digested by Bead Beater (Biospec Products, Barlesville. Okla.). The solution containing the digested fungal bodies was centrifuged (10,000×g, 15 minutes) and the supernatant was used as a crude enzyme solution. An ammonium sulfate precipitation and an ion exchange column chromatography were used for purification. The crude enzyme solution was saturated (85%) with ammonium sulfate. Dialysis by the precipitants obtained from the centrifugation (10,000×g, 15 minutes) was conducted overnight.

For the purification of the phytase, dialysis was conducted, and the resulting enzyme solution was adsorbed onto DEAE-Sepharose ion exchange column equilibrated with a buffer solution. Non-adsorbed protein was removed by washing with 50 mM sodium phosphate buffer solution (pH 7.0). NaCl solution with various concentrations (0.1 M, 0.3 M and 0.7 M) was applied to the column for the development, and the resulting fractions were used for the measurement of absorption at 280 nm.

Figure 9:
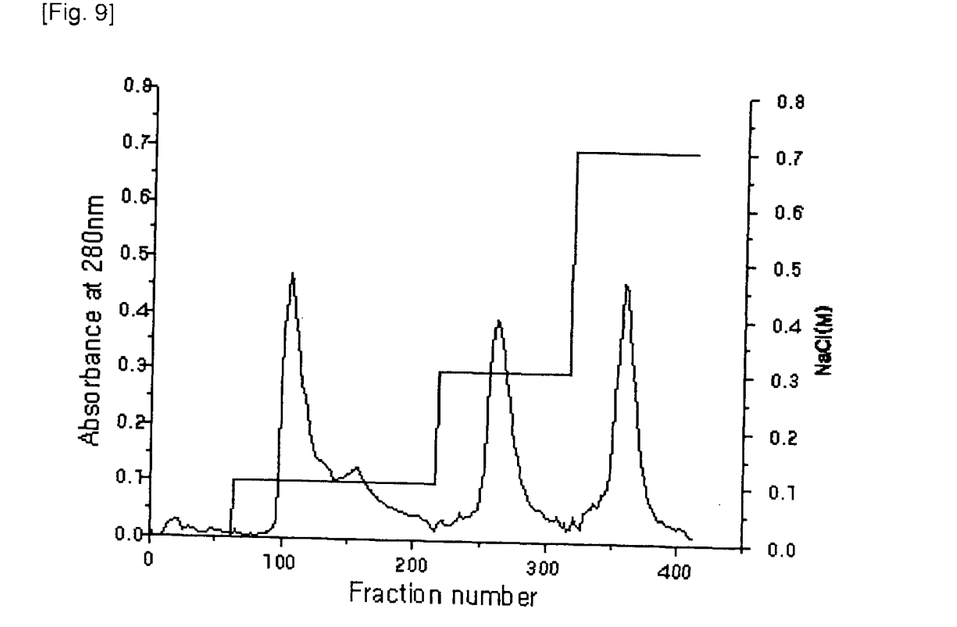
FIG. 9 shows the result of DEAE Sepharose ion exchange chromatography for the purifying the phytase from yeast cells of *Eballistra lineata* CM602 (KCTC 10945BP) strain.
Figure 10:
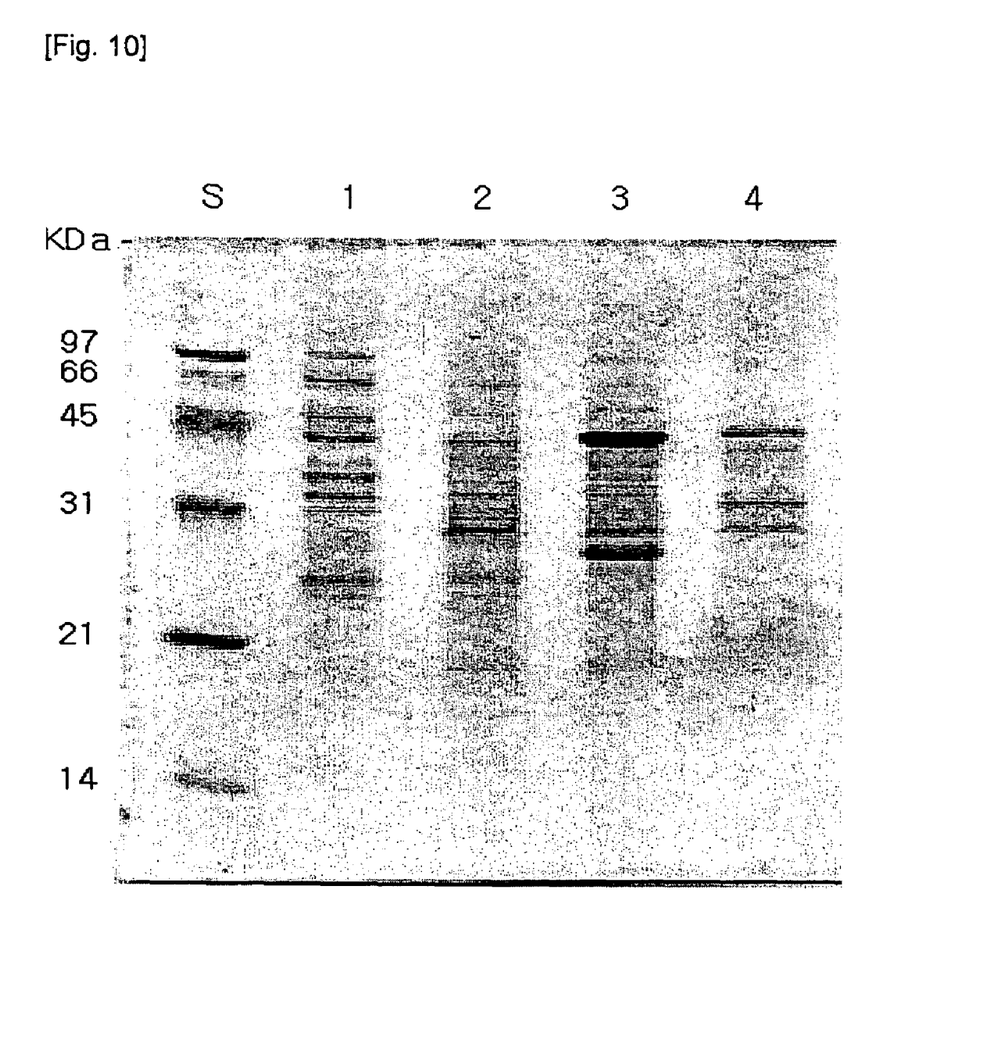
FIG. 10 shows the electrophoresis band patterns of the fraction obtained by the ion exchange chromatography.

The graph and the result of the electrophoresis are provided in FIGS. 9 and 10, respectively. As shown in FIG. 10, the developed portion (0.7 M) showed the highest phytase activity. The numbers in the electrophoresis image (FIG. 10) represents the followings.

| 1: Crude enzyme solution | 2: Developed portion (0.1 M) |
| 3: Developed portion (0.3 M) | 4: Developed portion (0.7 M) |

Figure 11:
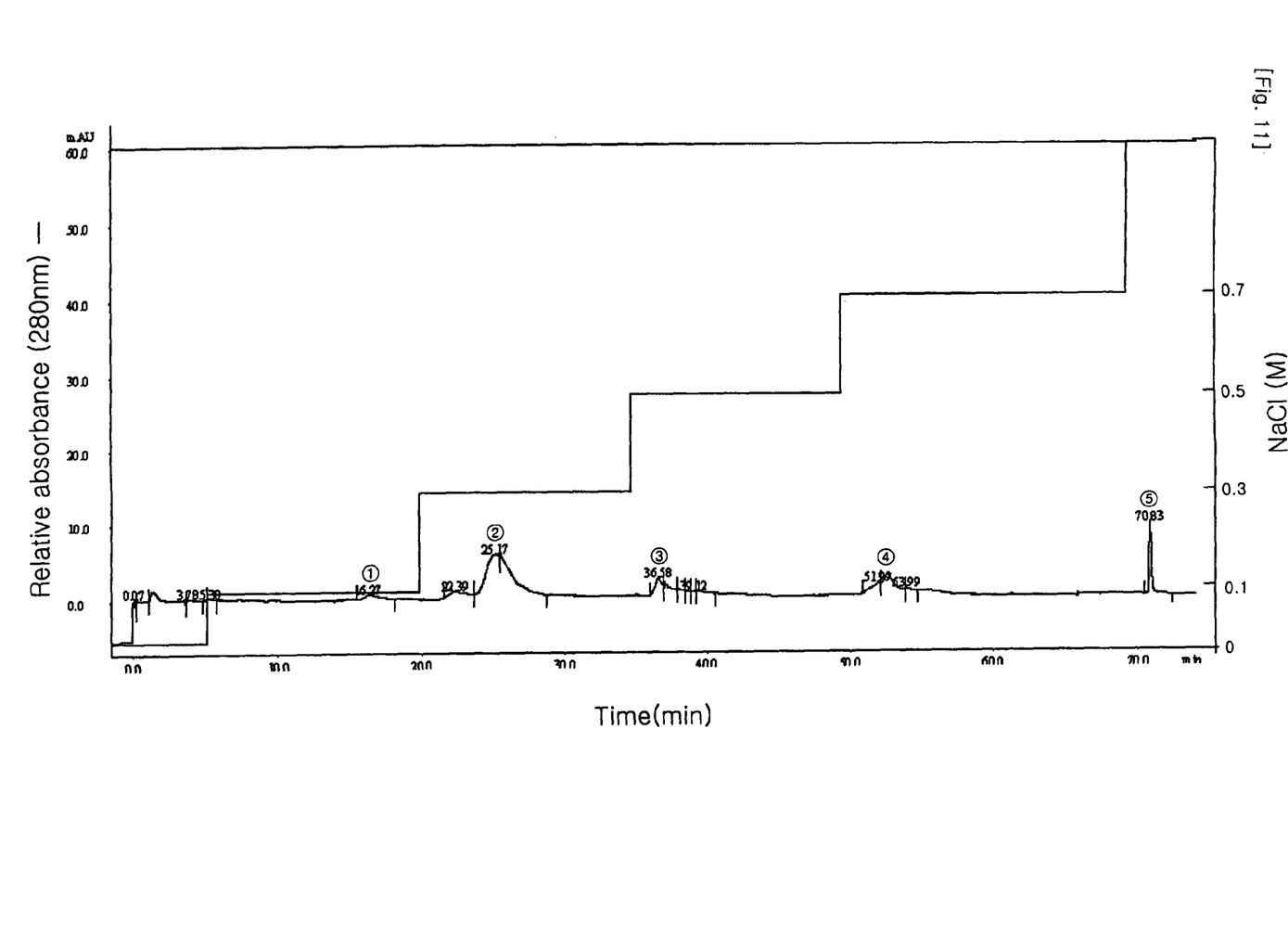
FIG. 11 shows the result of Mono Q ion exchange liquid chromatography for the purifying yeast cells of *Eballistra lineata* CM602 (KCTC 10945BP) strain.

Protein of this fraction was collected, freeze-dried and dissolved in a small amount of buffer solution. This solution was equilibrated with 50 mM sodium phosphate buffer solution (pH 7.0), and developed with each developing solution containing 0.1M, 0.3M, 0.5M and 0.7M of NaCl, respectively, at a rate of 80 mL/hour. AKTA FPLC system (Amersham Pharmacia Biotech, Uppsala, Sweden) equipped with a mono-Q 75S/S column for liquid chromatography was used in the purification. FIG. 11 is the resulting liquid chromatograph. The peak of No. 4 (0.5 M) shows an enzymatic activity.

As described above, the present invention provides a phytase-producing strain separated from dry pumpkin leaves, i.e. *Eballistra lineata* CM602 (KCTC 10945BP), and the phytase having different features from the conventional phytase.

It has not been reported that *Eballistra lineata* CM602 (KCTC 10945BP) produces a phytase, and it is noteworthy that a phytase herein shows a superior activity at a temperature around the body temperature of an animal and is thermo- and pH-stable. Therefore, a phytase herein is superior as an additive of forage which may increase the utilization of organic phosphorus.

Further, *Eballistra lineata* CM602 (KCTC 10945BP) strain may be used for a mass-production of enzyme by maximizing biosynthesis of phytase by means of gene recombination techniques, fermentation and optimization.

The invention claimed is:

1. A biologically pure strain of *Eballistra lineata* CM602 (KCTC 10945BP).

2. The strain of claim 1, which produces a phytase that is superior thermal stability and pH stability and shows a superior activity at 39° C.

3. A phytase, isolated from *Eballistra lineata* CM602 (KCTC 10945BP) of claim 1, wherein the phytase is purified by subjecting a crude phytase enzyme solution to dialysis, adsorbing the resulting enzyme solution onto ion exchange column equilibrated with a buffer solution, applying 0.7 M NaCl solution as a developing solution to the column, collecting and freeze-drying protein from the developed fraction, dissolving the protein in a buffer solution, and then further purifying the solution by using liquid chromatography using 0.5 M NaCl solution.

4. The phytase of claim 3, which shows the highest enzyme activity at 55° C., a sufficient enzyme activity at 39° C. and a superior thermal stability at 70° C.; and shows a relatively highest enzyme activity at pH of 7.0 and 2.0 and maintains more than 60% of relative activity at pH 3.5-9.0.

5. Forage comprising the phytase of claim 3.

* * * * *

SEQUENCE LISTING

```
<160> NUMBER OF SEQ ID NOS: 3

<210> SEQ ID NO 1
<211> LENGTH: 593
<212> TYPE: DNA
<213> ORGANISM: Eballistra lineata CM602 (KCTC 10945BP)
<220> FEATURE:
<221> NAME/KEY: rRNA
<222> LOCATION: (1)..(593)
<223> OTHER INFORMATION: Gene encodes ITS (internal transcribed spacer)
      rRNA

<400> SEQUENCE: 1
cggcgagtga agcgggaaga gctcaaattt gaaagctggc tcctttaggt gtccgcattg      60
taatctcgag aagcgttttc cgcgctggac cgcgtacaag tcccttggaa tagggcatcg     120
tagagggtga gaatcccgta cttgacgcgg cagccagtgc tttgtgatac gctctccacg     180
agtcgagttg tttgggaatg cagctcaaaa tgggtggtaa attccatcta aagctaaata     240
ttggggagag accgatagcg aacaagtacc gtgagggaaa gatgaaaagc actttggaaa     300
gagagttaaa cagtacgtga aattgtcgaa agggaagcgc ttgaagtcag ctatgttgtt     360
tggaattcag ccttgcttct gcatggtgta ctttccttgt aacaggccag catcggtttc     420
atcggccgga taagggtggg aggaatgtag catccttcgg gatgtgttat agcctcttac     480
tggatacggc tcgacgagac cgaggaacgc agtgcgccct cacgggtggg ccctcgggca     540
ccttcgcact taggatgctg gcgtaatggc tttaagcggc ccgtcttgaa aca            593
```

-continued

```
<210> SEQ ID NO 2
<211> LENGTH: 23
<212> TYPE: DNA
<213> ORGANISM: Eballistra lineata CM602 (KCTC 10945BP)
<220> FEATURE:
<221> NAME/KEY: misc_feature
<222> LOCATION: (1)..(23)
<223> OTHER INFORMATION: pITS forward primer

<400> SEQUENCE: 2
gtcgtaacaa ggttaacctg cgg                                              23

<210> SEQ ID NO 3
<211> LENGTH: 20
<212> TYPE: DNA
<213> ORGANISM: Eballistra lineata CM602 (KCTC 10945BP)
<220> FEATURE:
<221> NAME/KEY: misc_feature
<222> LOCATION: (1)..(20)
<223> OTHER INFORMATION: pITS reverse primer

<400> SEQUENCE: 3
tcctccgctt attgatatgc                                                  20
```